United States Patent
Ooyachi et al.

(10) Patent No.: US 9,346,735 B2
(45) Date of Patent: May 24, 2016

(54) METHOD FOR PRODUCING T-BUTANOL FROM ISOBUTANOL, METHOD FOR PRODUCING METHACROLEIN AND METHACRYLIC ACID FROM ISOBUTANOL, AND APPARATUS FOR PRODUCING THEM

(71) Applicant: MITSUBISHI RAYON CO., LTD., Tokyo (JP)

(72) Inventors: Ken Ooyachi, Hiroshima (JP); Toshiya Yasukawa, Hiroshima (JP); Shuji Akihara, Hiroshima (JP)

(73) Assignee: MITSUBISHI RAYON CO., LTD., Tokyo (JP)

( * ) Notice: Subject to any disclaimer, the term of this patent is extended or adjusted under 35 U.S.C. 154(b) by 0 days.

(21) Appl. No.: 14/356,168

(22) PCT Filed: Nov. 6, 2012

(86) PCT No.: PCT/JP2012/078714
§ 371 (c)(1),
(2) Date: May 5, 2014

(87) PCT Pub. No.: WO2013/069630
PCT Pub. Date: May 16, 2013

(65) Prior Publication Data
US 2014/0357890 A1    Dec. 4, 2014

(30) Foreign Application Priority Data
Nov. 7, 2011    (JP) .................................. 2011-243518

(51) Int. Cl.
| | | |
|---|---|---|
| *C07C 29/04* | (2006.01) | |
| *C07C 29/06* | (2006.01) | |
| *C07C 1/24* | (2006.01) | |
| *C07C 51/25* | (2006.01) | |
| *C07C 45/35* | (2006.01) | |
| *B01J 19/00* | (2006.01) | |
| *C07C 29/17* | (2006.01) | |

(52) U.S. Cl.
CPC ........... *C07C 51/252* (2013.01); *B01J 19/0046* (2013.01); *C07C 1/24* (2013.01); *C07C 29/04* (2013.01); *C07C 29/172* (2013.01); *C07C 45/35* (2013.01); *B01J 2219/00277* (2013.01); *C07C 2521/04* (2013.01); *C07C 2521/06* (2013.01); *C07C 2521/12* (2013.01)

(58) Field of Classification Search
CPC ...... C07C 29/04; C07C 29/06; C07C 29/172; C07C 51/152; B01J 19/0046
USPC ........................... 568/895, 896, 899; 560/205
See application file for complete search history.

(56) References Cited

U.S. PATENT DOCUMENTS

| | | | | |
|---|---|---|---|---|
| 6,111,145 | A | * | 8/2000 | Kobayashi .............. C07C 45/71 568/379 |
| 6,111,148 | A | * | 8/2000 | Ogawa et al. .................. 568/899 |
| 2005/0032639 | A1 | * | 2/2005 | Watanabe .............. B01J 23/002 502/302 |

FOREIGN PATENT DOCUMENTS

| | | | |
|---|---|---|---|
| JP | 48-32814 | * | 5/1973 |
| JP | 50-13308 | | 2/1975 |
| JP | 61-030538 | | 2/1986 |
| JP | 2000-044502 | | 2/2000 |
| WO | 99/33775 | | 7/1999 |
| WO | 03/053570 | | 7/2003 |

OTHER PUBLICATIONS

Taylor et al, Top Catal. (2010), vol. 53, pp. 1224-1230.*
Taylor et al, Top Catalysis (2010), vol. 53, pp. 1224-1230.*
"International Search Report (Form PCT/ISA/210)", mailed on Jan. 29, 2013, with English translation thereof, p. 1-p. 4.
Taylor et al., "Dehydration of Fermented Isobutanol for the Production of Renewable Chemicals and Fuels", Topics in Catalysis, May 2010, pp. 1224-1230, vol. 53.

* cited by examiner

*Primary Examiner* — Kamal Saeed
*Assistant Examiner* — Janet L Coppins
(74) *Attorney, Agent, or Firm* — Jianq Chyun IP Office

(57) ABSTRACT

A method for efficiently producing t-butanol as a raw material of a methacrylic resin from isobutanol is described, including a step (1) of dehydrating isobutanol to obtain butenes, and a step (2) of hydrating the butenes to obtain t-butanol. A method for producing methacrolein and methacrylic acid is also described, which further includes a step (3) of dehydrating and oxidizing the obtained t-butanol to obtain methacrolein and methacrylic acid. An apparatus for performing the steps (1) to (3) is also described.

8 Claims, No Drawings

METHOD FOR PRODUCING T-BUTANOL FROM ISOBUTANOL, METHOD FOR PRODUCING METHACROLEIN AND METHACRYLIC ACID FROM ISOBUTANOL, AND APPARATUS FOR PRODUCING THEM

CROSS-REFERENCE TO RELATED APPLICATION

This application is a 371 application of the International PCT application serial no. PCT/JP2012/078714, filed on Nov. 6, 2012, which claims the priority benefit of Japan application no. 2011-243518 filed on Nov. 7, 2011. The entirety of each of the above-mentioned patent applications is hereby incorporated by reference herein and made a part of this specification.

TECHNICAL FIELD

This invention relates to a method for producing t-butanol as a raw material of a methacrylic resin from isobutanol, in particular from isobutanol derived from biomass, a method for producing methacrolein and methacrylic acid from isobutanol, and an apparatus for producing them.

BACKGROUND ART

Conventionally, petroleum is used as a raw material of most plastics. In recent years, however, there is a concern regarding petroleum depletion and $CO_2$ generated on combustion of petroleum is a cause of global warming. Under the circumstances, chemicals derived from biomass that are referred to as carbon neutral recently attract attention as a substitute of petroleum.

Meanwhile, a methacrylic resin as a kind of plastics has an excellent characteristic such as transparency or weather resistance, and thus it is used for various applications. As a method for producing methacrolein or methacrylic acid, which is a raw material for methyl methacrylate as a raw material of a methacrylic resin, there is a catalytic gas phase oxidation method which uses t-butanol or isobutylene as a raw material.

Further, various methods for producing a raw material of a methacrylic resin have been conventionally known. For example, in Patent Literature 1 and Patent Literature 2, a method for producing t-butanol (tertiary butanol) from butenes is described. Further, in Patent Literature 3, a method for producing methacrolein from t-butanol is known. Further, in Patent Literature 4, a method for producing methacrolein and methacrylic acid from isobutylene is described. In Non-Patent Literature 1, a method for synthesizing isobutylene from isobutanol is described. Further, in Patent Literature 5, a method for producing methacrolein and methacrylic acid from isobutanol is described.

CITATION LIST

Patent Literature

Patent Literature 1: WO 99/33775 A
Patent Literature 2: JP 2000-44502 A
Patent Literature 3: JP 48-32814 A
Patent Literature 4: JP 50-13308 A
Patent Literature 5: JP 61-30538 A

Non-Patent Literature

Non-Patent Literature 1: Topics in Catalysis (2010) 53, 1224-1230

SUMMARY OF INVENTION

Technical Problem

However, all the conventional methods of Patent Literatures 1 to 4 described above for producing a raw material of a methacrylic resin are methods in which chemical products derived from petroleum are assumed as starting materials. In other words, there is no consideration regarding a specific subject of having a chemical product derived from biomass as a starting material.

t-butanol is not directly produced by a current fermentation method, but isobutanol can be obtained also by a fermentation method. In Non-Patent Literature 1, a study for isobutanol obtained by a fermentation method, and production of isobutylene as a raw material of a methacrylic resin by dehydrating isobutanol is described. However, there is no description about production of t-butanol. There is either no description relating to a treatment of impurities that exhibit an adverse effect on the reaction for producing a raw material of a methacrylic resin. In Patent Literature 5, a method for producing methacrolein and methacrylic acid from isobutanol is described, but the selectivity for the target product is extremely low. Thus, for efficient production of a raw material of a methacrylic resin, it is difficult to apply directly the conventional techniques that use chemical products derived from petroleum as starting materials.

This invention is achieved to solve the problems described above. Specifically, an object of this invention is to provide a method for producing efficiently t-butanol from isobutanol, a method for producing efficiently methacrolein and methacrylic acid from isobutanol, and an apparatus for producing them.

Solution to Problem

This invention relates to a method for producing t-butanol from isobutanol, being characterized by having:

a step (1) of dehydrating isobutanol to obtain butenes, and a step (2) in which of hydrating the butenes obtained from the step (1) to obtain t-butanol.

This invention also relates to a method for producing methacrolein and methacrylic acid from isobutanol, which is characterized by having:

a step (3) in which t-butanol obtained by the aforementioned method is dehydrated and oxidized to obtain methacrolein and methacrylic acid.

This invention further relates to an apparatus for producing t-butanol from isobutanol, which is characterized by having:

a device (A) for dehydrating isobutanol to obtain butenes, and a device (B) for hydrating the butenes obtained by the device (A) to obtain t-butanol.

This invention further relates to an apparatus for producing methacrolein and methacrylic acid, which is characterized by having:

a device (C) for dehydrating and oxidizing the t-butanol obtained by the aforementioned apparatus to obtain methacrolein and methacrylic acid.

Effects of this Invention

According to this invention, a method for producing efficiently t-butanol from isobutanol, a method for producing efficiently methacrolein and methacrylic acid from isobutanol, and their apparatuses can be provided. Further, because the reaction can be efficiently performed by having isobutanol derived from biomass as a starting material, in particular, it is very useful from the viewpoint of environmental protection.

DESCRIPTION OF EMBODIMENTS

The step (1) of this invention is dehydrating isobutanol to obtain butenes. The dehydration reaction of isobutanol can be performed by following a conventionally known method. It is particularly preferred to perform the reaction by using a dehydration catalyst like an acid catalyst. Specific examples of the acid catalyst include alumina, silica alumina, solid phosphate, titania, and zirconia. By using an acid catalyst including either one kind or two or more kinds of the examples, the dehydration reaction of isobutanol can be performed favorably. The reaction temperature is preferably 150 to 500° C.

It is sufficient as long as the device (A) used for the step (1) allows isobutanol to be dehydrated to obtain butenes. For example, it may be a device allowing that isobutanol is fed to a device filled with a dehydration catalyst to perform the dehydration reaction and butenes are collected as a reaction product.

In this invention, isobutanol is not directly used in a dehydration and oxidation step. Instead, the reaction is performed in an order that isobutanol is first converted to butenes in the step (1) and isobutylene in the butenes is hydrated in the step (2) to prepare t-butanol. Further, when the target product is methacrolein and methacrylic acid, the reaction is performed in an order that the t-butanol obtained in the step (2) is dehydrated and oxidized in the step (3) to give methacrolein and methacrylic acid. When isobutanol is directly used in a dehydration and oxidation step, butenes other than isobutylene as a by-product of the dehydration reaction exhibit an adverse effect on the catalyst and may cause a decrease in the yield or in the life of the catalyst. On the other hand, such adverse effect can be avoided in this invention. Specifically, because only isobutylene can be selectively hydrated among the butenes during the step (2) and t-butanol can be dehydrated at an approximately theoretical yield to form isobutylene and water during the step (3), there are substantially no butenes other than isobutylene present in the raw material supplied to the oxidation step. As such, the influence by butenes other than isobutylene, which is added to the catalyst of the oxidation step, can be avoided. In other words, regarding production of t-butanol from isobutanol and production of methacrolein and methacrylic acid from isobutanol, the dehydration and oxidation step can be performed with a good yield and the catalyst can be operated with long life in this invention.

Isobutanol used as a starting material of the step (1) is not particularly limited. However, in this invention, it is effective to use isobutanol derived from biomass, in particular. Isobutanol derived from biomass may contain a small amount of additional components other than isobutanol, for example alcohols and aldehydes. However, since the reaction is performed in a specific order as described above in this invention, the adverse effect caused by alcohols and aldehydes other than isobutanol can be avoided. Further, the isobutylene concentration in the butenes obtained by dehydrating isobutanol is generally higher than that in the butenes obtained from petroleum (10 to 55 mass %). Thereby, the efficiency of the step for hydrating butenes to t-butanol can be increased. Isobutanol derived from biomass indicates one obtained by using fermentable sugar of plant biomass such as corn and purifying it from the organic compounds obtained from the fermentation process. Such isobutanol derived from biomass can be also obtained as a commercially available product.

The step (2) of this invention is hydrating the butanes obtained in the step (1) to obtain t-butanol. Hydration of butenes can be performed with a conventionally known method, and, in particular, is preferably performed by using a hydration catalyst such as an acid catalyst. Specific examples of the acid catalyst include an ion exchange resin and heteropolyacid. More preferably, the acid catalyst is a strongly acidic cation exchange resin. By using an acid catalyst including either one kind or two or more kinds of the examples, the hydration reaction of the butenes can be performed favorably. The reaction temperature is preferably 30° C. and 100° C.

It is sufficient as long as the device (B) used for the step (2) allows butenes to be hydrated to obtain t-butanol. For example, it can be a device allowing that butenes are fed to a device filled with a hydration catalyst to perform the hydration reaction and t-butanol is collected as a reaction product.

The step (3) of this invention is dehydrating and oxidizing the t-butanol obtained in the step (2) to obtain methacrolein and methacrylic acid. The dehydration and oxidation of t-butanol can be performed with a conventionally known method, and, in particular, is preferably performed by using a dehydration catalyst such as an acid catalyst and an oxidation catalyst. Specific examples of the dehydration catalyst include those described for the step (1). However, when the oxidation catalyst also functions as a dehydration catalyst, it is not necessarily required to use a dehydration catalyst. Specific examples of the oxidation catalyst include those containing, as a catalyst component, at least molybdenum, bismuth, and iron. Such oxidation catalyst preferably has the composition represented by the following Formula (1).

$$Mo_aBi_bFe_cM_dX_eY_fZ_gSi_hO_i \qquad (1)$$

In the formula, Mo, Bi, Fe, Si, and O represent molybdenum, bismuth, iron, silicon, and oxygen, respectively. M represents at least one element selected from cobalt and nickel. X represents at least one element selected from chrome, lead, manganese, calcium, magnesium, niobium, silver, barium, tin, tantalum, and zinc. Y represents at least one element selected from phosphorus, boron, sulfur, selenium, tellurium, cerium, tungsten, antimony, and titanium. Z represents at least one element selected from lithium, sodium, potassium, rubidium, cesium, and thallium. a, b, c, d, e, f, g, h, and i represent the atomic proportions of the respective elements, and when a=12, b=0.01 to 3, c=0.01 to 5, d=1 to 12, e=0 to 8, f=0 to 5, g=0.001 to 2, h=0 to 20, and i is an atomic proportion of oxygen required for match the valences of the above components).

The concentration of t-butanol in the raw material gas can be modified within a broad range, but is preferably 1 to 20 vol %. As a molecular oxygen source, it is economically favorable to use air. However, if necessary, air enriched with pure oxygen can be also used. The molar ratio (volume ratio) between the reaction material and oxygen in the raw material gas is preferably in the range of 1:0.5 to 1:3. The raw material gas preferably contains water in addition to the reaction material and molecular oxygen, and is preferably used after dilution with an inert gas such as nitrogen or carbon dioxide. The moisture content in the raw material gas is preferably 1 to 45 vol %. The reaction pressure is preferably between normal pressure and several hundreds kPa. The reaction temperature can be generally selected within the range of 200 to 450° C. In particular, the range of 250 to 400° C. is preferred. Further, the contact time is preferably 1.5 to 15 seconds.

It is sufficient as long as the device (C) used for the step (3) allows t-butanol to be dehydrated and oxidized to obtain methacrolein and methacrylic acid. For example, it can be a device allowing that t-butanol is fed to a device filled with a dehydration catalyst and an oxidation catalyst (or oxidation catalyst only) to perform dehydration and oxidation and methacrolein and methacrylic acid are collected as a reaction product.

In the reaction product obtained by dehydration and oxidation of t-butanol in the step (3), most of t-butanol is converted into methacrolein and a part of the same is converted to methacrylic acid. The conversion to each of them can be suitably adjusted according to the reaction condition and the type of the catalyst.

For example, when the butenes obtained from the step (1) are directly used for the oxidation reaction of the step (3) (first-stage oxidation), the overall production process can be simplified. However, in such case, straight butenes other than isobutylene hardly react and remain in the gas produced, which exhibits an adverse effect on a subsequent step. In this regard, there is a method of adding a purification step before the catalytic gas phase oxidation of methacrolein (second-stage oxidation) is performed and returning a part of the unreacted butenes to the raw material gas, for example. However, in this method, straight butenes hardly react compared to isobutylene and thus are accumulated in the recycled gas, yielding lower isobutylene concentration in the raw material gas. Further, when the gas obtained from the step (3) (the reaction gas of the first-stage oxidation) is directly used as a raw material gas for catalytic gas phase oxidation (second-stage oxidation) without adding a purification step, the butenes can deactivate the catalyst of the second-stage oxidation, and therefore complete conversion of the butenes is necessary. However, as having a lower reactivity than isobutylene, the straight butenes remain without undergoing conversion under conditions showing a good yield in the conventional method, and deactivate the catalyst of the second-stage oxidation. On the other hand, such problem can be suppressed in this invention because only isobutylene among the butenes is selectively hydrated in the step (2).

Methacrolein is useful as a raw material of methacrylic acid. For example, with catalytic gas phase oxidation (second-stage oxidation) of methacrolein and a gas containing molecular oxygen (for example, air), methacrylic acid can be obtained. Further, with an esterification reaction between methacrylic acid and methanol, methyl methacrylate, which is one of the raw materials of a methacrylic resin, is obtained. By polymerizing methyl methacrylate, a methacrylic resin can be obtained.

EXAMPLES

Hereinbelow, this invention will be entered into details with reference to examples, but is not limited to those examples. The term "part" in the following descriptions means part by mass.

The raw material and the product were analyzed using gas chromatography. The conversion of the raw material (isobutanol, isobutylene, and t-butanol), and the selectivity of each component to be produced are defined as described below.

Conversion of raw material (%)=(Molar number of reacted raw material/Molar number of fed raw material)×100

Selectivity of each component (%)=(Molar number of each produced component/Total molar number of components detected by gas chromatography)×100

Example 1

Step (1): Dehydration of Isobutanol

A fixed-bed reactor filled with commercially available silica alumina (N6321HN•5 mmϕ×5 mm, produced by JGC C&C) as a dehydration catalyst was maintained at 340° C., and the reaction was allowed to occur by feeding, at space velocity of 45 s$^{-1}$, a mixture gas consisting of 5 vol % of isobutanol, 45 vol % of nitrogen, and 50 vol % of water vapor, thus obtaining a butene mixture gas (butenes). As a result, the conversion of isobutanol was 90.3%, and in the butene mixture gas, the isobutylene selectivity was 82.3%, the 1-butene selectivity was 5.8%, the cis-2-butene selectivity was 3.7%, the trans-2-butene selectivity was 5.8%, and the isobutane selectivity was 2.3%.

Step (2): Hydration of Butenes 1.0 part of the butene mixture gas obtained from the step (1) and 0.4 part of water were added to an autoclave, followed by addition of 5.0 parts of an ion exchange resin (Amberlyst 15JWET, produced by Dow Chemical Company). The reaction was then allowed to occur for 6 hours at 1.5 MPa and 60° C. As a result, the conversion of isobutanol was 92% and 1.04 parts of t-butanol were obtained. The content of sec-butanol as a byproduct was less than 500 ppm.

Step (3): Dehydration and Oxidation of t-Butanol

The t-butanol obtained from the step (2) was used, and dehydration and oxidation were performed thereto as follows to obtain methacrolein and methacrylic acid.

First, a fixed-bed reactor filled with commercially available silica alumina (N632HN•5 mm ϕ×5 mm, by JGC C&C) as a dehydration catalyst was maintained at 160° C., and the mixture gas consisting of t-butanol in a concentration of 10 vol % and 90 vol % of water vapor was reacted for a contact time of 3 seconds. As a result, the conversion of t-butanol was 91.2% and isobutylene was obtained with a high purity in a selectivity of 97.1%.

10 g of the oxidation catalyst was filled in a stainless reaction tube with an inner diameter of 15 mm. Then, the raw material gas consisting of 5 vol % of the isobutylene with a high purity that has been obtained by the above dehydration method, 12 vol % of molecular oxygen, 10 vol % of water vapor, and balance nitrogen gas was fed, and isobutylene was subjected to catalytic gas phase oxidation using molecular oxygen under conditions including atmospheric pressure, a contact time of 3.0 seconds, and a reaction temperature of 340° C. The proportions of the unreacted butenes and the reaction products in the obtained reaction gas are shown in Table 1.

Meanwhile, the oxidation catalyst used in the above step is one specifically produced by the following method. 500 parts of ammonium paramolybdate, 6.2 parts of ammonium paratungstenate, and 27.6 parts of cesium nitrate are dissolved and mixed in 1000 parts of pure water at 60° C. to prepare a liquid A. After that, 27.5 parts of bismuth trioxide were added to produce white precipitates in the liquid A. Meanwhile, separate from the above, 200.2 parts of ferric nitrate, 78.9 parts of nickel nitrate, 14.0 parts of zinc nitrate, and 357.1 parts of cobalt nitrate were added in order in 1000 parts of pure water to give a liquid B. Subsequently, the liquid B was added to the liquid A having white precipitates to give a liquid C in a slurry phase. After that, 24.1 parts of antimony trioxide were added to the liquid C to give a liquid D, which was aged for 1 hour at 80° C. followed by evaporation of most of water. The obtained cake-like material A was subjected to a heating treatment for 16 hours at 120° C. and further for 1 hour at 300° C. under air atmosphere followed by pulverization. After that, the press-molded product was crushed, and the crushed particles passing through a sieve with a mesh size of 2.36 mm and those not passing through a sieve with a mesh size of 0.71 mm were obtained. The classified particles with a specific size were again subjected to a heating treatment for 6 hours at 500° C. under air atmosphere to obtain a catalyst. The oxygen-excluded catalyst composition of the obtained catalyst was $Mo_{12}W_{0.1}Bi_{0.5}Fe_{2.1}Ni_{2.3}Co_{5.2}Zn_{0.2}Sb_{0.7}Cs_{0.6}$.

Comparative Example 1

In this Comparative Example, as a raw material for catalytic gas phase oxidation of isobutylene with molecular oxygen, a raw material gas consisting of 5 vol % of isobutylene, 0.4 vol % of 1-butene, 0.5 vol % of cis-2-butene, 0.4 vol % of trans-2-butene, 12 vol % of molecular oxygen, 10 vol % of water vapor, and 71.7 vol % of nitrogen was used.

Isobutylene was subjected to catalytic gas phase oxidation with molecular oxygen in the same manner as in Example 1 except that the aforementioned raw material gas is used. The proportions of the unreacted butenes and the reaction products in the obtained reaction gas are shown in Table 1.

TABLE 1

| | Proportions of major components [%] | | | | | |
|---|---|---|---|---|---|---|
| | Isobutylene | 1-butene | cis-2-butene | trans-2-butene | CO + CO2 | methacrolein + methacrylic acid |
| Example 1 | 5.1 | 0.0 | 0.0 | 0.0 | 5.9 | 85.6 |
| Comparative Example 1 | 8.7 | 5.8 | 5.4 | 6.6 | 4.0 | 66.9 |

Evaluation

As shown in Table 1, Example 1 relates to a method of producing methacrolein and methacrylic acid from isobutanol via the steps (1) to (3), and thus the proportion of methacrolein and methacrylic acid was high and the proportion of the residual butenes was low in the obtained reaction gas, wherein 1-butene, cis-2-butene, and trans-2-butene were not contained therein.

Meanwhile, since Comparative Example 1 relates to a method which is similar to a case in which a butene mixture gas produced by dehydration of isobutanol is directly used as a raw material for catalytic gas phase oxidation, the proportion of methacrolein and methacrylic acid was low and the proportion of the residual butenes was high in the obtained reaction gas, wherein a large amount of 1-butene, cis-2-butene, and trans-2-butene, which exhibited an adverse influence on the subsequent steps, were contained therein.

INDUSTRIAL APPLICABILITY

This invention is useful as a method for producing efficiently t-butanol as a raw material of a methacrylic resin, or methacrolein or methacrylic acid. Because the methacrylic resin has excellent transparency and weather resistance, it can be desirably used for various applications including a signboard, a cover of a lighting device, an aquarium tank, and recently a light guide plate of an LED liquid crystal television.

The invention claimed is:

1. A method for producing methacrolein and methacrylic acid, the method comprising:
    a step (1) of dehydrating isobutanol derived from biomass to obtain butenes containing more than 55 mass % of isobutylene;
    a step (2) of hydrating the butenes obtained from the step (1) to obtain t-butanol; and
    a step (3) of dehydrating and oxidizing the t-butanol obtained from the step (2) to obtain methacrolein and methacrylic acid.

2. The method according to claim 1, wherein an acid catalyst is used as a dehydration catalyst in the step (1).

3. The method according to claim 2, wherein the acid catalyst includes alumina, silica alumina, solid phosphate, titania, or zirconia.

4. The method according to claim 1, wherein an acid catalyst is used as a hydration catalyst in the step (2).

5. The method according to claim 4, wherein the acid catalyst includes an ion exchange resin or heteropolyacid.

6. The method according to claim 1, wherein an oxide including at least molybdenum, bismuth, and iron is used as an oxidation catalyst in the step (3).

7. An apparatus for producing methacrolein and methacrylic acid, comprising:
- a device (A) for dehydrating isobutanol derived from biomass to obtain butenes containing more than 55 mass % of isobutylene;
- a device (B) for hydrating the butenes obtained by the device (A), using an ion exchange resin as a hydration catalyst, to obtain t-butanol; and
- a device (C) for dehydrating and oxidizing t-butanol obtained by the device (B) to obtain methacrolein and methacrylic acid.

8. A method for synthesizing methyl methacrylate, comprising:
obtaining methacrylic acid by the method according to claim 1, and reacting the obtained methacrylic acid with methanol.

* * * * *